United States Patent
Klockgether et al.

(10) Patent No.: US 6,191,132 B1
(45) Date of Patent: Feb. 20, 2001

(54) USE OF QUISQUALATE RECEPTOR ANTAGONISTS

(75) Inventors: Thomas Klockgether, Gomaringen; Peter-Andreas Löschmann, Berlin; David Norman Stephens, Berlin; Lechoslaw Turski, Berlin; Helmut Wachtel, Berlin, all of (DE)

(73) Assignee: Schering Aktiengesellschaft, Berlin (DE)

( * ) Notice: Under 35 U.S.C. 154(b), the term of this patent shall be extended for 0 days.

(21) Appl. No.: 08/145,720

(22) Filed: Nov. 4, 1993

Related U.S. Application Data

(63) Continuation of application No. 07/810,009, filed on Dec. 20, 1991, now abandoned.

(30) Foreign Application Priority Data

Dec. 21, 1990 (DE) .................................. 40 41 981
Jun. 26, 1991 (DE) .................................. 41 21 483

(51) Int. Cl.$^7$ ..................... A61K 31/495; A61K 31/44; A61K 31/195; A61K 31/17
(52) U.S. Cl. .................... 514/249; 514/250; 514/282; 514/288; 514/567; 514/588
(58) Field of Search .................... 514/249, 250, 514/288, 567, 588, 282

(56) References Cited

U.S. PATENT DOCUMENTS

| | | | |
|---|---|---|---|
| 4,497,826 | * 2/1985 | Narabayashi et al. | 514/567 |
| 4,912,108 | 3/1990 | Jacobsen et al. | 514/250 |
| 4,948,794 | 8/1990 | Honore et al. | 514/249 |
| 4,977,155 | 12/1990 | Jacobsen et al. | 514/250 |
| 5,026,704 | 6/1991 | Honore et al. | 514/250 |
| 5,037,832 | * 8/1991 | Brumby et al. | 514/288 |
| 5,057,516 | 10/1991 | Jacobsen et al. | 514/250 |
| 5,061,706 | 10/1991 | Honoreé et al. | 514/249 |

FOREIGN PATENT DOCUMENTS

| | | |
|---|---|---|
| 0 260 467 | 3/1988 | (EP) . |
| 0 283 959 | 9/1988 | (EP) . |
| WO 90/15606 | 12/1990 | (WO) . |

OTHER PUBLICATIONS

M.J. Sheardown et al., "2,3–Dihydroxh–6–nitro–7–sulfamoyl–benzo(F) quinoxaline: A Neuroprotectant for Cerebral Ischemia," Science, vol. 247, No. 4942, Feb. 2, 1990, pp. 571–574.

J.E.F. Reynolds, editor, "Martindale: The Extra Pharmacopoeia," 29th edition, London: The Pharmaceutical Press, 1989, No. 4541–g, "Levodopa", pp. 1015–1020.

J.W. Olney et al., "Brief Communication: Excitotoxicity of L–DOPA and 6–OH–DOPA: Implications for Parkinson's and Huntington's Diseases," Experimental Neurology, vol. 108, No. 3, Jun. 1990, pp. 269–272.

T. Klockgether et al., "The AMPA Receptor Antagonist NBQX has Antiparkinsonian Effects in Monoamine–depleted Rats and MPTP–treated Monkeys," Annals of Neurology, vol. 30, No. 5, Nov. 1991, pp. 717–723.

P.–A. Löschmann et al., Synergism of the AMPA–antagonist NBQX and the and the NMDA–antganist CPP with L–Dopa in Models of Parkinson's Disease, Journal of Neural Transmission, P–D Sect., vol. 3, 1991, pp. 203–213.

* cited by examiner

*Primary Examiner*—Kevin E. Weddington
(74) *Attorney, Agent, or Firm*—Millen, White, Zelano & Branigan, P.C.

(57) ABSTRACT

The new use of antagonists of the AMPA receptor complex and its physiologically compatible salts as pharmaceutical agents for prevention and treatment of Parkinson's disease as well as pharmaceutical agents, which contain these compounds, is described.

21 Claims, No Drawings

USE OF QUISQUALATE RECEPTOR ANTAGONISTS

This application is a continuation of application Ser. No. 07/810,009, filed Dec. 20, 1991, now abandoned.

BACKGROUND OF THE INVENTION

The invention relates to the new use of antagonists of the quisqualate receptor complex or its physiologically compatible salts as pharmaceutical agents for the prevention and treatment of Parkinson's disease, as well as pharmaceutical agents which contain these compounds and their combination with anti-Parkinson's agents with synergistic action.

In the central nervous system of mammals, including humans, high concentrations of excitatory amino acids, such as glutamate and aspartate, are present (Fonnum, F., J. Neurochem. 42: 1–11, 1984). For the excitatory amino acids, various receptors exist, which are identified according to their specific agonists as N-methyl-D-aspartate (NMDA) receptor, kainate (KA) receptor and quisqualate (QUIS) receptor. The quisqualate receptors are also named AMPA receptors according to the specific agonists (RS)-2-amino-3-hydroxy-5-methyl-4-isoxazolepropionate. The synaptic function of the excitatory amino acid L-glutamate is mainly imparted by AMPA receptors.

From clinical and animal-experimental findings, there are indications that in the case of Parkinson's disease (PD), increased glutamatergic neurotransmission in various nuclei of the basal ganglia results as a result of the striatal deficiency of dopamine. The neostriatum (NEO) represents the input structure of the basal ganglia: it obtains a massive glutamatergic projection from the cortex and the dopaminergic nigrostriatal pathway, which degenerates in the case of PD, from the substantia nigra pars compacta (SNC). From the NEO, there are direct pathways to the output nuclei of the basal ganglia, the internal pallidum link (GPi) and the substantia nigra pars reticulata (SNR), as well as indirect pathways, which run through the outer pallidum link (GPe) and the subthalamic nucleus (STH). The STH receives a direct glutamatergic innervation of its own from the cortex; its neurons projecting to the output nuclei also use L-glutamate as a transmitter.

The synaptic functions of dopamine in the NEO are complex. Its effect on the striatal neurons projecting to the GPe is mainly inhibitory, so that as a result of the striatal dopamine deficiency, as it is present in the case of PD, the excitatory glutamatergic influences on these neurons predominate. Since both the striatal pathway to the GPe, and the pathway projecting to the STH starting from there are inhibitory, in the case of PD in the STH the phenomenon of the disinhibition results with the increase of the tonic cellular activity. By its glutamatergic projections, the STH finally produces a pathologically increased neuronal activity in the output nuclei of the basal ganglia. Tests on animal models of the PD show that after administration of dopaminergic substances, a normalization of the increased excitatory neurotransmission results, which runs parallel to the "clinical" improvement.

SUMMARY OF THE INVENTION

Surprisingly, it has been discovered that quisqualate receptor antagonists inhibit the pathologically increased neuronal activity and block the glutamatergic transmission in the NEO, STH and the output nuclei of the basal ganglia and therefore are usable as pharmaceutical agents for the treatment of PD. Accordingly, the invention comprises a method for the treatment or prevention of Parkinson's Disease, comprising administering to a host an effective amount of a quisquilate receptor antagonist.

Because of their action mechanism, quisqualate receptor antagonists also have a neuroprotective effect, in particular also relative to the possible neurotoxic effects, which are triggered by dopaminergic pharmaceutical agents, which can be administered in combination with QA receptor antagonists. They can therefore also be used as pharmaceutical agents for preventive treatment of PD.

According to the invention, compounds or their physiologically compatible salts, which have a high affinity to the central AMPA receptors and selectively offset the synaptic effects of quisqualate, are suitable. Such quisqualate receptor antagonists are described, for example, in EP-A-374 534, EP-A-348 872 (U.S. Pat. Nos. 4,977,155 and 5,057,516), EP-A-283 959 (U.S. Pat. Nos. 4,889,885 and 4,912,108), EP-A-377 112 (U.S. Pat. No. 5,061,706), and EP-A-315 959 (U.S. Pat. Nos. 4,948,794 and 5,026,704). Quinoxaline and quinoxalinedione derivatives with selective and nonselective effects on AMPA receptors, such as quinoxalinedione derivatives and their tautomeric forms of Formula I

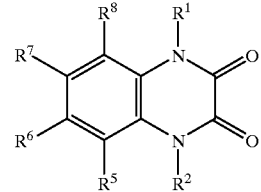

(I)

in which $R^1$ and $R^2$ each represent hydrogen or one of the substituents mentioned in the cited patents, and $R^5$, $R^6$, $R^7$, and $R^8$ are the same or different, and each means hydrogen, $NO_2$, $NH_2$, cyano, halogen (fluorine, chlorine, bromine, or iodine), $CF_3$, $SO_2NR'R'$ $SO_2R'$ or $OR'$ and R' is hydrogen or $C_{1-4}$-alkyl, or $R^5$ and $R^6$ or $R^7$ and $R^8$ together mean a fused-to benzene or hetaryl ring or $(CH_2)_4$, and the benzene or hetaryl radical can be substituted one to three the same or different with $NO_2$, $NH_2$, cyano, halogen, $CF_3$, $SO_2NR'R'$, $SO_2R'$, or $OR'$ and R' has the above meaning. Suitable hetaryl rings are pyridine, pyrazole, thiophene, pyrazine, triazole, imidazole, suitable substituents $R^1$ and $R^2$ are $C_{1-12}$-alkyl, $C_{3-8}$-cycloalkyl, $C_{4-8}$-cycloalkylalkyl, $C_{6-10}$-aryl, especially phenyl, $C_{7-11}$-aralkyl, especially benzyl, $C_{2-7}$-alkanoyloxy, hydroxy, $C_{1-6}$-alkoxy, $C_{6-10}$-aryloxy, especially phenoxy, $C_{7-11}$-aralkyl, especially benzyloxy, $C_{3-8}$-cycloalkyloxy, $C_{4-8}$-cycloalkylalkyloxy and $C_{1-12}$-alkyl substituted by hydroxy, $NH_2$, carboxy, carboxylic acid esters, or carbocyclic acid amines.

Especially suitable are quinoxalinedione and benzoquinoxalinedione derivatives and their tautomeric forms and salts with selective and non-selective effect on AMPA receptors which optionally are substituted once to twice with halogen, $NO_2$, cyano, $CF_3$, $SO_2NR'R'$, $SO_2R'$ or $OR'$ and R' is hydrogen or $C_{1-4}$-alkyl and $R^1$ and $R^2$ each represent hydrogen or a substituent. Compounds such as 6-nitro-7-sulfamoyl-benzo[f]-quinoxaline-2,3-(1H,4H)-dione (NBQX), 6,7-dinitroquinoxaline-2,3-dione (DNQX) and 6-cyano-7-nitroquinoxaline-2,3-dione (CNQX) are particularly suitable.

The physiologically compatible salts are derived from alkali or alkaline-earth metals or the usual inorganic or organic acids, such as hydrochloric acid, hydrobromic acid, sulfuric acid, phosphoric acid, citric acid, maleic acid or fumaric acid.

As a result of the blocking of the central AMPA receptors, i.e., the structures, which with Parkinson's disease exhibit an increased neuronal activity, compounds with selective and nonselective effect on AMPA receptors are suitable both for symptomatic treatment of Parkinson's disease and for combining with usual anti-Parkinson's agents, such as L-DOPA, L-DOPA in combination with benserazide and dopaminergic agonists, such as, for example, lisuride, bromocryptine, amantadine derivatives, memantine and its derivatives and compounds such as those described in EP-A-351 352 (U.S. Pat. No. 5,037,832).

By combining the pharmaceutical agents according to the invention with usual anti-Parkinson's agents, the dose to be administered of the usual pharmaceutical agent is reduced and its effect is increased.

Because of the test results, the quisqualate receptor antagonists used according to the invention also have a neuroprotective effect, which prevents the degeneration of dopaminergic neurons, in particular relative to the possible neurotoxic effects, which are caused by the usual anti-Parkinson's agents. The absence of psychotomimetic side effects is also advantageous.

The invention also comprises pharmaceutical agents, which contain said compounds, their production as well as the use of the compounds according to the invention for production of pharmaceutical agents, which are used for treatment and prophylaxis of the above-mentioned diseases. For example, agents of the invention may be prophylactically administered to persons in a group having a defined risk of contracting Parkinson's Disease, e.g., persons with cognitive or motor defects which are a preindication of the disease, or persons at the average age of onset (55–60 years) having a family history of the disease. One of ordinary skill in the art could readily identify such groups for whom prophylactic treatment is indicated.

The pharmaceutical agents are produced according to processes known in the art, by the active ingredient being brought together with suitable vehicles, auxiliary agents and/or additives into the form of a pharmaceutical preparation, which is suitable for enteral or parenteral administration. The administration can take place orally or sublingually as a solid in the form of capsules or tablets or as a liquid in the form of solutions, suspensions, elixirs or emulsions or rectally in the form of suppositories or optionally also in the form of subcutaneously usable injection solutions. As auxiliary agents for the desired pharmaceutical agent formulation, the inert organic and inorganic vehicles known to one skilled in the art are suitable, such as, for example, water, gelatin, gum arabic, lactose, starch, magnesium stearate, talc, vegetable oils, polyalkylene glycols, etc. Optionally, preservatives, stabilizers, wetting agents, emulsifiers or salts for changing the osmotic pressure or buffers can further be comprised.

The pharmaceutical preparations can be present in solid form, for example, as tablets, coated tablets, suppositories, capsules or in liquid form, for example, as solutions, suspensions or emulsions.

As vehicle systems, interface-near auxiliary agents, such as salts of the bile acids or animal or plant phospholipids, but also mixtures of them as well as liposomes or their components can also be used.

For oral application, in particular tablets, coated tablets or capsules with talc and/or hydrocarbon vehicles or binders, such as, for example, lactose, corn or potato starch, are suitable. The application can also take place in liquid form, such as, for example, as juice, to which a sweetener optionally is added.

The dosage of the active ingredients can vary depending on the method of administration, age and weight of the patient, type and severity of the disease to be treated and similar factors. The daily dose is 0.001–1 g/kg body weight, and the dose can be given as a single dose to be administered once or subdivided into 2 or more daily doses.

In the combination preparations according to the invention with synergistic effect, the active ingredients can be present in a combined formulation or else administered simultaneously or successively in separated formulations, and the total dose may be administered once or is divided into several doses.

The daily dose of the active ingredients in the combination preparations is 2 mg to 1500 mg for the usual anti-Parkinson's agent and 1 mg to 500 mg for the quisqualate receptor antagonist, doses of 5 mg to 100 mg are especially suitable.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German P 40 41 981.9, filed Dec. 21, 1990, and German P 41 21 483.8, filed Jun. 26, 1991, are hereby incorporated by reference.

EXAMPLES

The effect according to the invention is shown, with 6-nitro-7-sulfamoylbenzo[f]-quinoxaline-2,3(1H,4H)-dione in the following tests:

The tests were performed on male Wistar rats (Schering AG, Berlin, FRG) with a weight between 220 and 240 g. They were kept under controlled conditions with free access to food and water. All tests took place between 1000 and 1400 hours. The measurements began 5 minutes after the administration of the substance and were performed for 60 minutes.

All substances were administered intraperitoneally (i.p.) in a volume of 0.5 ml per kilogram of body weight. Control animals received a corresponding volume of physiological common salt solution. The following substances were used: reserpine, α-methyl-p-tyrosine, benserazide and 6-nitro-7-sulfamoylbenzo[f]quinoxaline-2,3-(1H,4H)-dione (NBQX). Reserpine was dissolved in one drop of glacial acetic acid and diluted with demineralized water. Benserazide and α-methyl-p-tyrosine were dissolved in physiological common salt solution. NBQX was brought into solution with a small amount of 1 N NaOH and then diluted with physiological common salt solution. The pH was adjusted to 7.4.

A computerized Digiscan-16 system (Omnitech, Columbus, Ohio, U.S.A.) was used to measure the locomotor activity. Each measurement of activity consists of a plexiglass cage (40×40×40 cm), which is surrounded by 48 horizontal and vertical infrared sensors. The total number of light barrier breaks was measured as a measurement of the locomotor activity.

The tonic electromyogram (EMG) activity was derived from the M. gastrocnemius-soleus (GS) of conscious rats with the help of teflon-insulated wire electrodes. The animals were placed for this purpose in ventilated plexiglass boxes, so that their hind legs hung out through slots in the bottom of the boxes. The electric signals were amplified, filtered (5 Hz–10 kHz) and rectified. The integrated EMG activity was averaged over periods of 5 minutes each. The spontaneous activity of the reserpinized animals before administration of the substances was measured in 2 segments and was used as an initial value.

For triggering of contralateral rotations on unilaterally substantia nigra lesioned rats, male Wistar rats were lesioned 8 months before the experiment by injection of 16 micrograms of 6-hydroxydopamine (6-OHDA) in the left substantia nigra. The measurement of the rotations took place in automated rotometers. The animals were placed in plexiglass half-shells (diameter 40 cm) and mechanically connected with an incremental angle-position encoder. The clockwise and counterclockwise movements were detected separately in 10 minute intervals for 2 hours.

The results of these tests can be summarized as follows:

In normal rats, NBQX (10–30 mg/kg i.p.) results in no increase of locomotion. The emptying of the central monoamine storage by pretreatment with reserpine (5 mg/kg i.p. 24 hours before the experiment) and α-methyl-p-tyrosine (250 mg/kg i.p. 4 hours before the experiment) brings about a massive reduction of the normal locomotion, which can be offset again by L-DOPA (50–150 mg/kg i.p.) (in combination with benserazide, 100 mg/kg i.p.) in a dose-dependent way. NBQX (5–30 mg/kg i.p.) does not increase the locomotor activity of reserpinized rats. If, however, NBQX (5 mg/kg o.p.) is combined with L-DOPA (50–150 mg/kg i.p.), a leftward displacement of the L-DOPA dose-effect curve is produced so that a steady effect can be achieved with less than half the L-DOPA.

The tonic EMG activity of rats reserpinized in the GS represents a quantitative measurement of the muscular rigidity. It can be suppressed by L-DOPA (50–150 mg/kg i.p.) in a dose-dependent way (FIG. 4). NBQX (5–30 mg/kg i.p.) has a similar, but shorter effect. If threshold doses of NBQX (5 mg/kg i.p.) and L-DOPA (50 mg/kg i.p.), each of which by itself has no influence on the EMG activity, are combined, this results in a complete suppression of the EMG activity.

In dosages of 0.78, 3.13 and 12.5 mg/kg i.p., neither contralateral nor ipsilateral rotations are to be triggered by NBQX. On the other hand, after pretreatment with benserazide (100 mg/kg i.p.—15 minutes), L-DOPA (25, 50 and 100 mg/kg i.p.) results in a dose-dependent induction of contralateral rotation. In combined treatment with a threshold dose of L-DOPA (25 mg/kg i.p.) and NBQX (12.5 mg/kg i.p.), a dose which has an inhibitory effect per se, a significant induction of contralateral rotations can be observed.

In the same model, NBQX (0.39, 1.56, 6.25 mg/kg i.p.) was tested with the direct dopaminergic agonist apomorphine (0.05 mg/kg i.p.) or lisuride (0.1 mg/kg i.p.). Here too, the combined treatment results in a significant synergism (analysis of variance and Tukey test, *p<0.05, **p<0.01).

NBQX was tested in the same way on true marmosets, in which a Parkinson's syndrome had been produced by the neurotoxin MPTP. These monkeys, like the Parkinson patient, show a great reduction of mobility. For the experiments described here, the animals were placed in cages, which were equipped with infrared light barriers. The number of the light barrier breaks was recorded automatically and as a measurement, the mobility was measured over 2 hours.

Groups of 4 animals were treated either with a solvent, 20 mg/kg of L-DOPA and 20 mg/kg of benserazide, 6.25 mg/kg of NBQX or a combination of L-dopa, benserazide and NBQX in the same dosages. The selected dose of L-dopa had no effect. NBQX by itself inhibited the mobility, while the combination treatment resulted in a statistically significant stimulation of the locomotor activity in the meaning of a synergism. In another experiment, the same dose of L-dopa and benserazide was combined with various doses of NBQX (0.39; 1.56; 6.25 mg/kg i.p.). It was able to be shown here that the effect of NBQX is dose-dependent.

These tests show that antagonists of the AMPA receptors in dosages, which by themselves are without effects, increase the effect of L-DOPA on the akinesia and muscular rigidity of reserpinized rats after systemic administration. Also, the effect of L-DOPA is increased in the 6-OHDA rotation model and on the MPTP lesioned primates.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method for the treatment of Parkinson's Disease, comprising administering to a host an effective amount of quisqualate receptor antagonist in combination with a dopaminergic agonist.

2. A method according to claim 1, wherein the quisqualate receptor antagonist is a quinoxaline or quinoxalinedione compound.

3. A method according to claim 2, wherein the quisqualate receptor antagonist is 6-nitro-7-sulfamoyl-benzo[f]-quinoxaline-2,3(1H,4H)-dione, 6,7-dinitroquinoxaline-2,3-dione or 6-cyano-7-nitroquinoxaline-2,3-dione.

4. A method according to claim 1, wherein the dopaminergic agonist is lisuride, bromocryptine, apomorphine, amantadine or memantine.

5. A method according to claim 1, wherein the quisqualate receptor antagonist is administered in combination with L-3,4-dihydroxyphenyl-alanine or in combination with both L-3,4-dihydroxyphenyl-alanine and benserazide.

6. A pharmaceutical composition comprising effective amounts of a quisqualate receptor antagonist and:
   (a) a dopaminergic agonist;
   (b) L-3,4-dihydroxyphenyl-alanine; or
   (c) L-3,4-dihydroxyphenyl-alanine and benserazide.

7. A pharmaceutical composition according to claim 6, comprising effective amounts of a quisqualate receptor antagonist and lisuride, bromocryptine, apomorphine, amantadine or memantine.

8. A pharmaceutical composition according to claim 6, wherein the quisqualate receptor antagonist is 6-nitro-7sulfamoyl-benzo[f]-quinoxaline-2,3(1H,4H)-dione, 6,7-dinitroquinoxaline-2,3-dione or 6-cyano-7-nitroquinoxaline-2,3-dione.

9. A method according to claim 1, wherein the amount of dopaminergic agonist is about 2–1500 mg/kg and the amount of quisqualate receptor antagonist is about 1–500 mg/kg.

10. A method according to claim 1, wherein the amount of dopaminergic agonist is about 50–150 mg/kg and the amount of quisqualate receptor antagonist is about 5–100 mg/kg.

11. A method according to claim 1, wherein the amount of dopaminergic agonist is about 50–150 mg/kg and the amount of quisqualate receptor antagonist is about 5–30 mg/kg.

12. A composition according to claim 6, wherein the amount of (a), (b) or (c) is about 2–1500 mg/kg and the amount of quisqualate receptor antagonist is about 1–500 mg/kg.

13. A composition according to claim 6, wherein the amount of (a), (b) or (c) is about 50–150 mg/kg and the amount of quisqualate receptor antagonist is about 5–100 mg/kg.

14. A composition according to claim 6, wherein the amount of (a), (b) or (c) is about 50–150 mg/kg and the amount of quisqualate receptor antagonist is about 5–30 mg/kg.

15. A method for the treatment of Parkinson's disease, comprising administering to a host an effective amount of a dopaminergic agonist and a quisqualate receptor antagonist of formula I

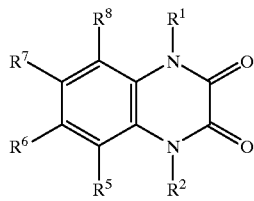

wherein
$R^1$ and $R^2$ are each independently hydrogen, halogen, CN, $NH_2$, $NO_2$, $SO_3H$, $SO_2NH_2$, $CONH_2$, OH, alkoxy, aryloxy, aralkoxy, cycloalkyloxy, allyloxy, or $C_{1-12}$-alkyl optionally substituted by OH, formyl, carboxy, a carboxylic ester, a carboxylic amide, a carboxylic amine, $C_{3-8}$-cycloalkyl, $C_{5-8}$-aryl or $C_{5-8}$-aralkyl, $R^5$, $R^6$, $R^7$ and $R^8$ are each independently hydrogen, $NO_2$, $NH_2$, cyano, halogen, $CF_3$, $SO_2NR'R'$, $SO_2R'$ or $OR'$, in which $R'$ is hydrogen or $C_{1-4}$-alkyl, or $R^5$, $R^6$, $R^7$ and $R^8$ together mean a fused-to-benzene or hetaryl ring or $(CH_2)_4$, said benzene or hetaryl radical optionally independently substituted one to three times by $NO_2$, $NH_2$, cyano, halogen, $CF_3$, $SO_2NR'R'$, $SO_2R'$ or $OR'$.

16. A method according to claim 15, wherein $R^1$ or $R^2$ is hydroxy, methoxy, propenyloxy, cyclohexyloxy, carboxymethyloxy, benzyloxy, carbamoyl, piperdino, amino, phenyl or $OCOR^3$, in which $R^3$ is $C_{1-2}$-alkyl, ethoxy, phenoxy or phenyl.

17. A method according to claim 15, wherein the quisqualate antagonist is 6-nitro-7-sulfamoyl-benzo[f]-quinoxaline-2,3-(1H,4H)-dione and the dopaminergic agonist is L-3,4-dihydroxyphenyl-alanine, apomorphine or lisuride.

18. A pharmaceutical composition according to claim 6, comprising 6-nitro-7-sulfamoyl-benzo[f]-quinoxaline-2,3-(1H,4H)-dione and L-3,4-dihydroxyphenyl-alanine, apomorphine or lisuride.

19. A method according to claim 1, wherein the amounts of the quisqualate receptor antagonist and the dopaminergic agonist employed are such that the anti-Parkinson effect is greater than additive.

20. A method according to claim 15 wherein the amounts of the quisqualate receptor antagonist and the dopaminergic agonist employed are such that the anti-Parkinson effect is greater than additive.

21. A composition according to claim 6, wherein the amounts of the quisqualate receptor antagonist and (a), (b) or (c) are such that the pharmacological effect is greater than additive.

* * * * *